(12) United States Patent
Rai et al.

(10) Patent No.: US 7,790,134 B1
(45) Date of Patent: Sep. 7, 2010

(54) METHOD OF PURIFYING ISOSACCHARINATE

(75) Inventors: Dhanpat Rai, Yachats, OR (US); Robert C. Moore, Edgewood, NM (US); Mark D. Tucker, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 150 days.

(21) Appl. No.: 12/047,351

(22) Filed: Apr. 2, 2008

Related U.S. Application Data

(62) Division of application No. 10/465,315, filed on Jun. 18, 2003, now abandoned.

(51) Int. Cl.
*C09K 3/00* (2006.01)

(52) U.S. Cl. .................................. 423/430; 562/400

(58) Field of Classification Search ................ 423/430; 562/400
See application file for complete search history.

(56) References Cited

U.S. PATENT DOCUMENTS

| | | | | |
|---|---|---|---|---|
| 4,824,588 A | * | 4/1989 | Lin | 252/70 |
| 7,514,493 B1 | * | 4/2009 | Moore et al. | 524/457 |

* cited by examiner

*Primary Examiner*—Steven Bos
(74) *Attorney, Agent, or Firm*—Robert D. Watson; Jeffrey D. Myers

(57) ABSTRACT

A method of purifying isosaccharinate by mixing sodium carbonate, potassium carbonate, sodium hydroxide or potassium hydroxide with calcium isosaccharinate, removing the precipitated calcium carbonate and adjusting the pH to between approximately 4.5 to 5.0 thereby removing excess carbonate and hydroxide to provide an acidic solution containing isosaccharinate.

9 Claims, 9 Drawing Sheets

METHOD OF PURIFYING ISOSACCHARINATE

This application is a divisional application of application Ser. No. 10/465,315 filed Jun. 18, 2003, now abandoned, which is incorporated herein by reference.

GOVERNMENT RIGHTS

The Government has rights to this invention pursuant to Contract No. DE-AC04-94AL85000 awarded by the U.S. Department of Energy.

BACKGROUND OF THE INVENTION

1. Field of the Invention (Technical Field)

The present invention relates to decontamination methods and kits for decontaminating surfaces contaminated with actinides, other radionuclides, or heavy metals.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Although solutions of varying effectiveness exist for decontaminating surfaces contaminated with actinides, other radionuclides, and/or heavy metals, existing solutions often have limited effectiveness or pose additional environmental risks.

The main ingredients of past decontamination solutions have been complexing agents such as EDTA and citrate. Unfortunately, these reagents have a limited efficiency in the range of pH values of environmental interest. Most existing technologies are expensive, use harsh chemicals, are hazardous to workers, and create secondary mixed wastes that are not environmentally acceptable.

The use of isosaccharinate ("ISA") or isosaccharinic acid ("HISA") as a decontamination reagent overcomes many of these difficulties. Throughout the specification and claims, unless otherwise clear from context, "ISA" is used to refer to either of isosaccharinate or isosaccharinic acid. The past available data on ISA with tetravalent actinides have been very limited (limited to pH 12), empirical, and only related to determining actinide behavior in cementitious environments. ISA has heretofore been seen only as a danger to containment of radionuclides because it is a degradation byproduct of cellulose. Extensive work has been, done on characterizing and managing this danger. See, e.g., G. Fanger, et al., "Project SAFE: Complexing Agents in SFR", Swedish Nuclear Fuel and Waste Management Company Report R-01-04 (2001); K. Vercammen, et al., "Complexation of Th(IV) and Eu(III) by α-isosaccharinic acid under alkaline conditions", *Radiochim. Acta* 89:393-401 (2001); K. Vercammen, et al., "Evidence for the Existence of Complexes between Th(IV) and α-isosaccharinic Acid under Alkaline Conditions", *Radiochim. Acta* 84:221-224 (1999); K. Vercammen, "Complexation of Calcium by α-Isosaccharinic Acid under Alkaline Conditions", *Acta Chemica Scandinavica* 53:241-246 (1999); D. Rai, et al., "The Influence of isosaccharinic Acid on the Solubility of Np(IV) Hydrous Oxide", *Radiochim. Acta* 83:9-13 (1998); D. Rai, et al., "Solubility of Crystalline Calcium Isosaccharinate", *J. Solution Chemistry* 27:1109-1122 (1998); S. Holgersson, et al., "Effects of Gluco-isosaccharinate on Cs, Ni, Pm and Th Sorption onto, and Diffusion into Cement", *Radiochim. Acta* 82:393-398 (1998); E. Wieland, et al., "Interaction of Eu(III) and Th(IV) with sulphate-resisting Portland cement", Mat. Res. Soc. Symp. Proc. 506:573-578 (1997); L. van Loon, et al., "Sorption of isosaccharinic Acid, a Cellulose Degradation Product, on Cement", *Environmental Science & Technology* 31:4:1243-1245 (1997); X. Bourbon, et al., "Influence of Organic Degradation Products on the Solubilisation of Radionuclides in Intermediate and Low Level Radioactive Wastes", *Radiochim. Acta* 74:315-319 (1996); G. Baston, et al., "Sorption of Plutonium and Americium on Repository, Backfill and Geological Materials Relevant to the JNFL Low-Level Radioactive Waste Repository at Rokkasho-Mura", Mat. Res. Soc. Symp. Proc. 353:957-964 (1995); B. Greenfield, et al., "The Identification and Degradation of Isosaccharinic Acid, a Cellulose Degradation Product", Mat. Res. Soc. Symp. Proc. 353:1151-1158 (1995); A. Moreton, "Thermodynamic Modelling of the Effect of Hydroxycarboxylic Acids on the Solubility of Plutonium at High pH", Mat. Res. Soc. Symp. Proc. 294:753-758 (1993); and E. Wieland, et al., "Immobilisation of Strontium, Nickel, and Iodide by a Sulphate-Resisting Portland Cement. 13 Radiochemical Conference, Czech Republic, p. 388 (1998).

The present invention is of decontamination methods and kits employing ISA, as well as of an improved method of making ISA. Although ISA forms strong complexes with all different oxidation states of actinides, the complexes it forms especially with tetravalent actinides are of the highest interest. This is because actinides (especially Pu and Th) are expected to be present in the tetravalent state, the state at which they are extremely insoluble and need to be removed for decontamination purposes. The present invention relates, therefore, in large part to decontamination via the tetravalent actinide complexes of ISA. Therefore, the present application presents: 1) fundamental data on ISA complexes with tetravalent actinides, in particular Th(IV) and Np(IV), in the entire range of pH values of environmental interest, so that comparisons can be made of its efficiency with the existing cleaning agents (e.g., EDTA and citrate); and 2) refined ISA preparation and purification techniques, so that large quantities of ISA can be produced cheaply and quickly, presenting a major advantage over other complexing agents which may work equally well in a limited range of pH values (e.g., siderophores) but which cannot be synthesized inexpensively.

ISA is environmentally friendly, easily biodegraded, and strongly chelates many metal ions in different oxidation states; therefore, it can be used in applications other than decontamination of radioactive contaminated surfaces. The ISA can be used alone, in addition to, or as an additive in cleaning products and solvents. This includes but is not limited to the use of ISA in solutions, foams, creams, powders, or other formulations and forms for cleaning and surface preparation (e.g., removal of metal ions). Additionally, ISA can be used alone or with other chelators such as citrate, EDTA, other organic/inorganic chelators and solvents, surfactants, cleaning agents, and wetting agents in cleansing formulations such as detergents, soaps, and metal stain removers. These other specific applications for which ISA-containing products can be used include: 1) radioactive decontamination of soils as in soil washing, soil flushing, leaching agent for soils in place or in a process where the soils are decontaminated in an above ground process; 2) decontamination of plants, animals, people, live stock, and buildings, because ISA is environmentally friendly and easily biodegradable; and 3) metal stain removal (e.g., iron, calcium, and rust) and decontamination agent for fabrics, steel, wood, concrete, leather, stone, marble, and glass, and other manmade materials.

SUMMARY OF THE INVENTION

Disclosure of the Invention

The present invention is of a method of treating (decontaminating) a metal-contaminated surface, comprising: providing an ISA-containing substance to the surface; and removing the ISA-containing substance from the surface. In the preferred embodiment, The ISA-containing substance is a foam, gel, or solution, and may additionally contain one or more of the following: non-ISA organic chelators, inorganic chelators, carbonates, oxidizers, anti-freezes, and surfactants. The method removes one or more metals selected from actinides, other radionuclides, heavy metals, iron, and calcium. The ISA is in one or more forms selected from calcium, sodium, and potassium forms.

The present invention is also of a method for preparing ISA acidic solution, comprising: preparing a solution of $X_2CO_3$ and XOH; adding $Ca(ISA)_2$ to the solution; allowing reaction in the solution to generate solid $CaCO_3$ and dissolved X(ISA); removing solid $CaCO_3$ precipitate from the solution; and adjusting pH of the solution to between approximately 4.5 to 5.0 to remove excess carbonate and hydroxide; where X is Na or K. Allowing reaction preferably comprises agitating the solution. An additional step of adding $CaCl_2$ to the ISA solution to pH between approximately 4.5 to 5.0 to reprecipitate $Ca(ISA)_2$ may be employed, preferably with subsequent washing of the reprecipitated $Ca(ISA)_2$. The steps of the method may then be repeated using the reprecipitated $Ca(ISA)_2$ one or more times to increase purity of the solution and/or precipated $Ca(ISA)_2$.

The invention is additionally of a method for preparing alkaline solution of ISA, comprising: preparing $Ca(ISA)_2$ in aqueous suspension; adding XOH to the suspension; allowing reaction in the suspension to generate solid $Ca(OH)_2$ and dissolved X(ISA) in solution; and removing solid $Ca(OH)_2$ precipitate from the solution; where X is selected from the group consisting of Na and K. The second adding step produces a final pH of between approximately 13.8 and 14.3. The first adding step comprises adding $Ca(ISA)_2$ to water to no greater than the solubility limit of the X(ISA).

The invention is further of a kit for decontaminating metal-contaminated surfaces, the kit comprising X(ISA), where X is selected from one or more of Na and K. The X(ISA) may be in dissolved or solid form.

Objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DESCRIPTION OF THE PREFERRED EMBODIMENTS

Figure 1:
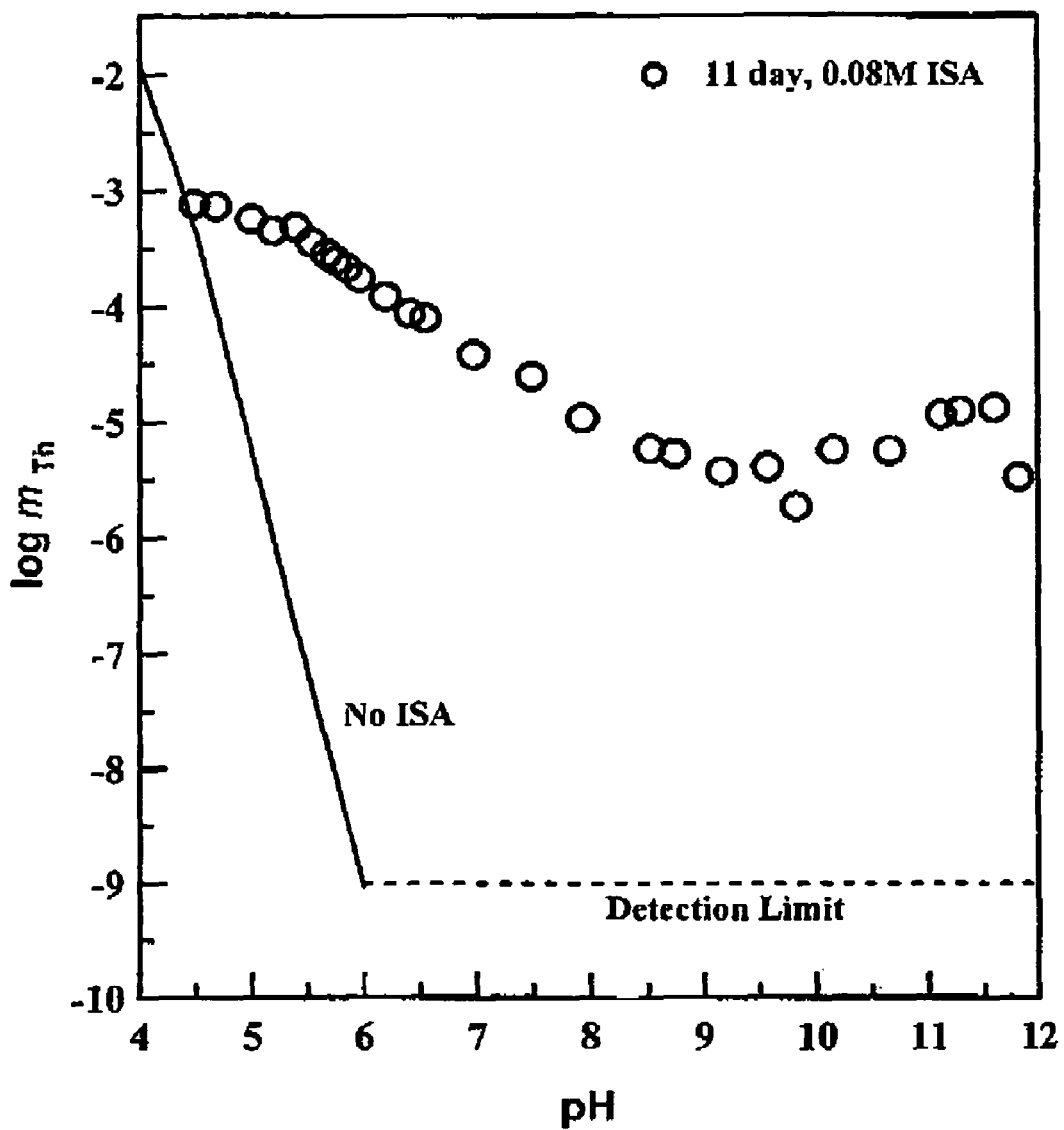
FIG. 1 is a graph of aqueous Th concentration in equilibrium with $ThO_2(am)$ as a function of pH in the presence and absence of ISA.

Best Modes for Carrying Out the Invention

The present invention is of a new and efficient radionuclide and heavy metal decontamination method and kit employing isosaccharinic acid ("HISA") or isosaccharinate ("ISA"), preferably deployed in a biodegradable foam, gel, or solution. The invention is useful for actinide and other radionuclide and heavy metal decontamination of steel, concrete and other surfaces.

The formula for ISA is as follows: $C_5H_{11}O_4COO^-$. ISA can be produced by the reaction of strong bases with cellulose or $Ca(OH)_2$ with α-lactose. In its sodium or potassium form, ISA is highly soluble in water. Other reagents similar to ISA might be substituted for ISA, but the data on these compounds is limited. Such compounds include tetrahydroxypentanoic acid ($C_4H_9O_4COOH$) and gluconate ($C_5H_{11}O_5COO^-$).

Incorporated into a gel, foam or solution, ISA can be used for removing radionuclides from surfaces by chelating the radionuclides and increasing their water solubility. ISA can be used alone or with other compounds that aid in decontamination. For example carbonates, oxidizers, surfactants, antifreezes, or other organic chelators such as citrate, EDTA, oxalate, etc., can also be added to increase the effectiveness of the ISA based decontamination foam of the invention. When the ISA-containing substance is removed from the surface, such as by washing with water, the surface is thereby decontaminated.

The typical manner in which ISA acts on an actinide, other radionuclide, or heavy metal is as follows:

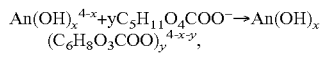
$$An(OH)_x^{4-x} + yC_5H_{11}O_4COO^- \rightarrow An(OH)_x(C_6H_8O_3COO)_y^{4-x-y},$$

where An is any actinide, radionuclide, or heavy metal.

ISA can also be added to other decontamination solutions, gels, or foams to enhance their effectiveness for decontamination of materials contaminated with radionuclides or heavy metals. ISA can be used in the calcium, sodium, potassium, or other forms. ISA can be added to other materials used for decontamination, such as strippable coatings, sprays, and the like.

The pH values of aqueous foams according to the invention are preferably adjusted based on the surfaces the foam will be applied to. For example, pH values of foams to be applied to Fe containing surfaces will be adjusted from slightly acidic to near neutral conditions. The ISA concentration will be maintained to as high a concentration as 0.2 M, depending on the contaminant to be removed and its concentration and type and concentration of the matrix elements. Similar considerations apply to gels and solutions according to the invention.

The present invention is also of a process for purification of $Ca(ISA)_2$ and conversion to the sodium or potassium form for inexpensively producing ISA and for conversion to forms that can be easily incorporated into products such as foams and gels for decontamination use.

A common method for producing calcium isosaccharinate (Ca-ISA) is by the hydrolysis reaction of α-lactose using $Ca(OH)_2$ (R. L. Whistler, et al., in *Methods in Carbohydrate Chemistry Volume II, Reactions of Carbohydrates*, edited by R. L. Whistler et al., pp. 477-479 (Academic Press, London, 1963)). This method, however, produces a product with significant impurities, mainly $CaCO_3$ and unreacted $Ca(OH)_2$. The product thus produced is also fairly insoluble and would have to be converted to a more soluble form for use as a decontaminating agent.

The present invention provides a method to produce high quality $Ca(ISA)_2$ and to convert this to a more soluble form. The method for purification of $Ca(ISA)_2$ is rapid, not very labor intensive, and produces $Ca(ISA)_2$ of very high purity. The method proceeds as follows for an exemplary desired amount of $Ca(ISA)_2$:

1) Add 0.25 moles $Ca(ISA)_2$ (such as prepared by the Whistler et al., 1963 method) to one liter of solution containing 0.35 moles $Na_2CO_3$ and 0.01 M NaOH.

2) Shake mixture (typically an hour is sufficient). The $Na_2CO_3$ reacts with $Ca(ISA)_2$ to produce solid $CaCO_3$ and Na(ISA) solution.

3) Filter or centrifuge out $CaCO_3$ that has precipitated to separate it from the Na(ISA) and residual $Na_2CO_3$ and NaOH solution.

4) Adjust pH to between 4.5 to 5.0 using HCl to get rid of excess carbonate and hydroxide.

5) Add $CaCl_2$ to reprecipitate $Ca(ISA)_2$.

6) Wash the precipitate and repeat the above steps if end product of highest quality is desired. In most cases, one time through steps 1 to 5 is adequate.

Figure 9:
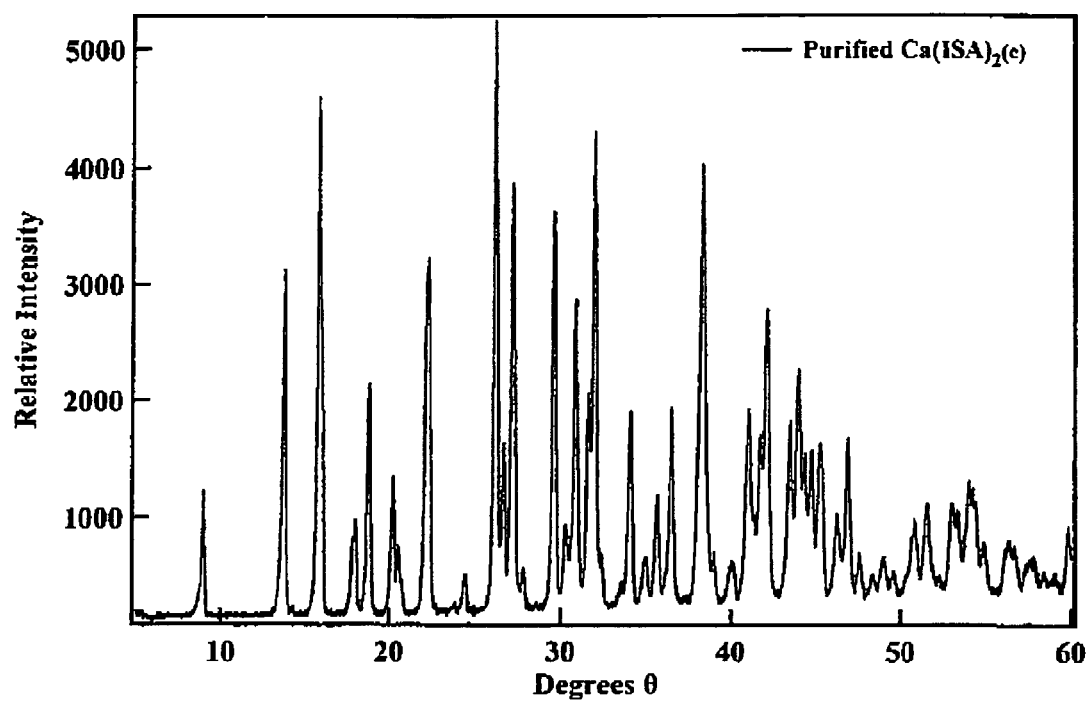
FIG. 9 shows X-ray diffraction patterns of the purified $Ca(ISA)_2$ according to the invention; the absence of diffraction peaks for $CaCO_3$, $Ca(OH)_2$, lactose monohydrate (which could result during preparation) indicates the sample to be free of detectable amounts of these impurities.

The solids can be recovered by evaporation, freeze-drying, or other procedures. Freeze drying is most efficient and loses the least material and produces product of consistent quality (greater than 99% purity). This has been shown using a combination of X-ray diffraction analyses of the $Ca(ISA)_2$ and total chemical analyses. The X-ray diffraction analyses show the absence of peaks for α-lactose and $Ca(OH)_2$, the reactants, and for $CaCO_3$ that can form as an impurity during preparation of $Ca(ISA)_2$ (see FIG. 9).

To convert $Ca(ISA)_2$ to the more soluble sodium or potassium forms, the following procedure may be employed:

a) Add $Ca(ISA)_2$ to water to the solubility limit of Na(ISA).

b) Add sufficient NaOH or KOH to form Na(ISA) or K(ISA) in solution to make sure that a sufficient excess amount of hydroxide is present to produce a final pH of about 14.2 (acceptably between 13.8 and 14.3).

c) Shake mixture (typically overnight is sufficient).

d) NaOH or KOH reacts with $Ca(ISA)_2$ to precipitate $Ca(OH)_2$ and produce solutions containing Na(ISA) or K(ISA) with a portion of unreacted NaOH or KOH. Filter to remove $Ca(OH)_2$ precipitate.

e) Na(ISA) or K(ISA) is now in solution.

An alternate procedure for producing Na(ISA) solution is to follow the steps 1 through 4 above. To produce K(ISA) solution, follow steps 1 through 4 above with substitution of $K_2CO_3$ for $Na_2CO_3$. This procedure produces an end product of the highest purity. The chemical analyses of these solutions have shown that the concentration of Ca, the only expected deletrious impurity, is only about 0.01%.

To summarize, ISA can be used as a decontamination agent, especially for actinides but also for several other radionuclides and heavy metals as well as a cleaning agent for multiple purposes. The use of ISA over other organic acids for decontamination has several advantages, including:

ISA strongly complexes with actinides in the tetravalent state in the entire range of pH values of environmental interest, whereas other organic chelators such as citrate and EDTA have a limited applicability range. ISA is also more effective in the presence of iron-containing materials and those containing concrete than currently used agents (such as EDTA), and thus is effective in cleaning soils, metallic surfaces, concretes, and buildings.

ISA is an effective agent for actinides in other oxidation states, other radionuclides, and removing stains.

ISA can be used in a decontamination solution, foam, gel, or other media that is not highly acidic or basic and therefore will not harm the material to be decontaminated.

Using the purification method of the invention, large quantities of highly pure ISA can be economically produced. Since ISA works by complexing with actinides, a pure form of ISA will perform best. Also, the conversion of ISA to the soluble sodium or potassium form is necessary to get a sufficient amount of ISA in water to use in decontamination.

ISA is manufacturable from common, inexpensive chemicals.

ISA is biodegradable and environmentally friendly.

INDUSTRIAL APPLICABILITY

The invention is further illustrated by the following non-limiting examples.

Example 1

The results from solution decontamination experiments are given in Table 1 for plutonium. Coupons of roof asphalt (roofing shingles) and steel were contaminated by placing 0.1 ml of a plutonium solution onto the coupon surfaces. The surfaces were air dried and placed in glass beakers containing 100 ml of water, 5% Na(ISA) solution, 5% M sodium citrate or 5% ETDA solution all at an initial pH of 6.0. The solutions were gently agitated and the liquid was sampled over time. The solutions and coupons were analyzed using liquid scintillation. The results for plutonium indicate the ISA removed 17% more Pu from the asphalt coupons than the water or EDTA solutions.

TABLE 1

Results from solution experiments for the decontamination of Pu contaminated asphalt roof shingles. 15 min. contact time with solutions.

| Deconta-mination agent | Initial Pu on sample $\mu Ci$ | Pu is solution after 15 min. $\mu Ci/ml$ | Pu is solution after 30 min. $\mu Ci/ml$ | Total % of Pu removed by decon agent |
|---|---|---|---|---|
| Water | 6 | 0 | 0 | 0 |
| 5% EDTA solution | 6 | .164 | .246 | 24.6% |
| 5% ISA solution | 6 | .254 | .412 | 41.2% |

Example 2

The results from solution decontamination experiments are given in Table 2 for uranium. Coupons of roof asphalt (roofing shingles) and steel were contaminated by placing 0.1 ml of an uranium solution onto the coupon surfaces. The surfaces were air dried and placed in glass beakers containing 100 ml of water, 5% Na(ISA) solution, 5% M sodium citrate or 5% ETDA solution all at an initial pH of 6.0. The solutions were gently agitated and the liquid was sampled over time. The solutions and coupons were analyzed using liquid scintillation. The results for uranium in the +4 and +6 oxidation states indicate that ISA was much more effective than citrate, a common biodegradable decontamination agent.

TABLE 2

Removal of U(IV) and U(VI) from steel coupons using solutions of citric acid and ISA

| | Conc. of U in solution 15 min. | Conc. of U in solution 30 min. | Conc. of U in solution 45 min. | Conc. of U in solution 60 min. | % U removed |
|---|---|---|---|---|---|
| U(IV) | | | | | |
| Water | 1.68 | 2.91 | 3.01 | 2.19 | <1% |
| 5% Citrate solution | 3 | 6 | 8.7 | 11.3 | 2% |
| 5% ISA solution | 49.1 | 51.4 | 58 | 79.6 | 15% |
| U(VI) | | | | | |
| Water | 0 | 0 | 0 | 0 | 0 |
| 5% citric acid solution | 2.59 | 4.37 | 6.78 | 8.3 | 1% |
| 5% ISA solution | 226 | 269 | 403 | 419 | 92% |

Example 3

In coupon experiments with Pu contaminated steel and wood, the effectiveness of ISA incorporated into a gel decontamination foam was tested. Pu was deposited onto the steel and wood coupons and they were allowed to dry for 3 days.

EDTA and ISA were incorporated into a $SiO_2$ based gel. 5 g of the gels were placed on the coupons and allowed to sit for 15 min. The gels were then removed using a small cotton wipe and tested for Pu by liquid scintillation. The results are given in Table 3. The results indicate that the ISA performed better than EDTA for both steel and wood decontamination.

TABLE 3

Results from decontamination of Pu contaminated steel coupons using water, citric acid and ISA. Pu is in the +4 oxidation state when placed on the coupons.

| Surface | Decontamination agent | Initial Pu on surface | Pu in decon gel | % Decon-tamination |
|---|---|---|---|---|
| Steel | Water based gel only | 6 $\mu Ci$ | 0 $\mu Ci$ | 0% |
| Steel | 5% EDTA gel | 6 $\mu Ci$ | 33 $\mu Ci$ | 55% |
| Steel | 5% ISA gel | 6 $\mu Ci$ | 5.1 $\mu Ci$ | 85% |
| Wood | Water based gel only | 6 $\mu Ci$ | $1 \times 10^{-4}$ $\mu Ci$ | <1% |
| Wood | 5% EDTA gel | 6 $\mu Ci$ | 1.92 $\mu Ci$ | 32% |
| Wood | 5% ISA gel | 6 $\mu Ci$ | 2.45 $\mu Ci$ | 41% |

Example 4

Figure 2:
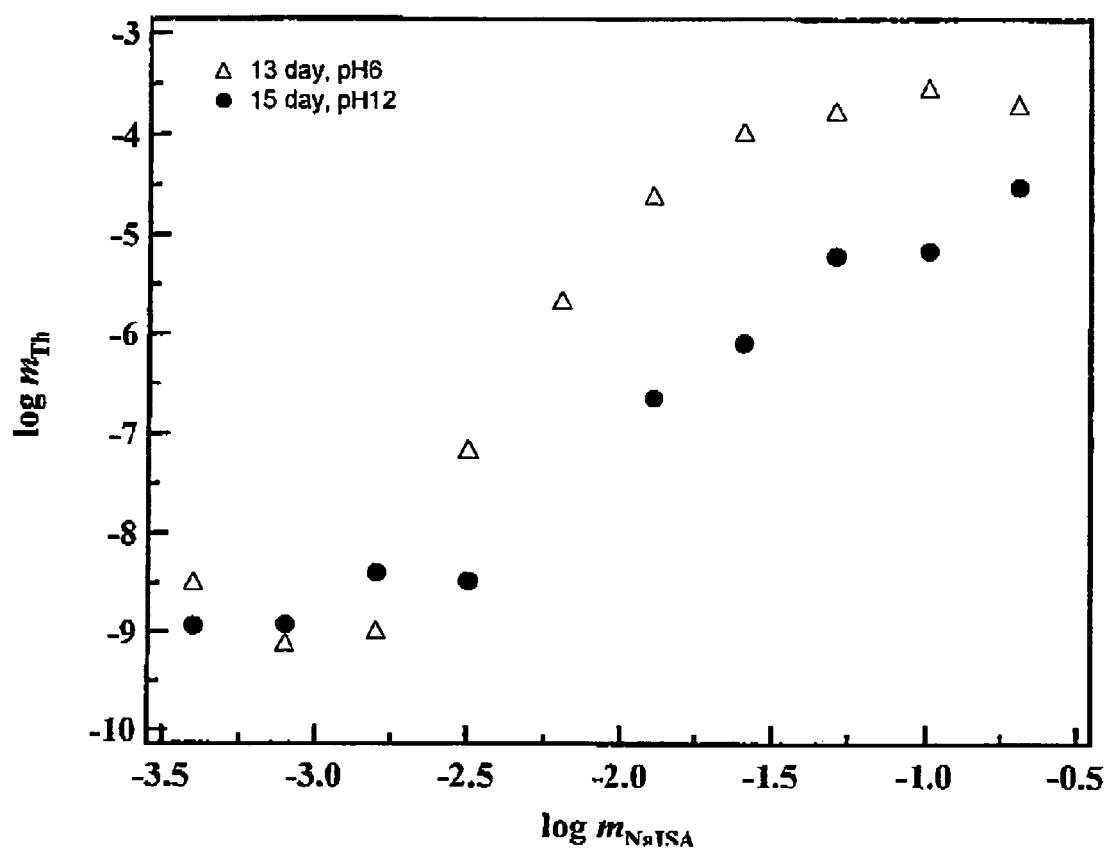
FIG. 2 is a graph of aqueous Th concentration in equilibrium with $ThO_2(am)$ as a function of ISA concentrations and at a fixed pH values of 6 and 12.

The Th concentrations in equilibrium with $ThO_2(am)$, a Th compound that forms readily under environmental conditions and is an excellent analog for expected behavior of other tetravalent actinides, as a function of pH shows that the observed aqueous Th concentrations in the presence of ISA are up to many orders of magnitude higher than expected in the absence of ISA (FIG. 1), indicating that ISA is effective in removing Th from contaminated surfaces in a large range of pH values. Although the solubility data shown in FIG. 1 was obtained at a fixed concentration of 0.08 M ISA, the amount of Th solubilized will increase with the increase in ISA concentrations. To further develop the fundamental data and quantify ISA's ability to solubilize Th from contaminated surfaces, $ThO_2(am)$ solubility was determined as a function of ISA concentrations and at fixed pH values of 6 and 12 (FIG. 2). These data show a dramatic increase in Th concentrations with the increase in ISA concentrations, thereby confirming the results presented in FIG. 1 that ISA is an effective decontaminating agent for Th in a wide range of pH values of environmental concern. These data (FIG. 2) also show that at the given ISA concentration it is slightly more effective in the acidic region.

Figure 3:
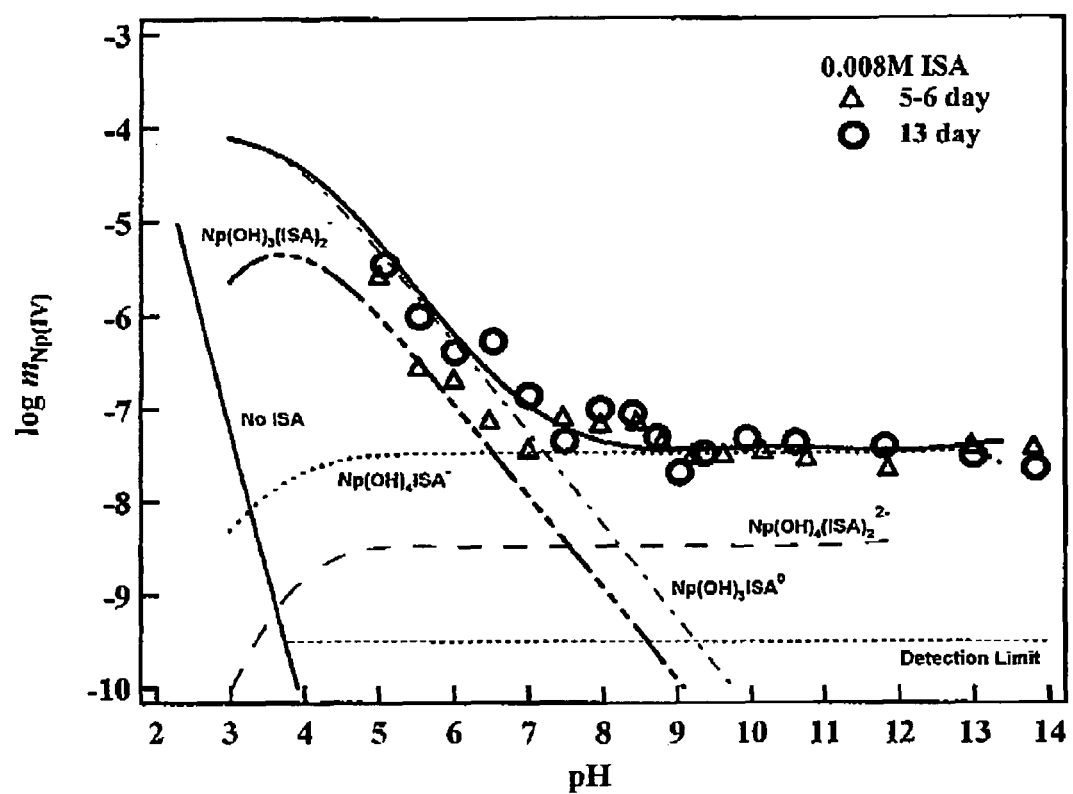
FIG. 3 is a graph of aqueous Np(IV) concentrations in equilibrium with $NpO_2(am)$ as a function of pH and in the presence and absence of ISA, showing the effectiveness of ISA in solubilizing Np(IV) in a large range of pH values and depicting the fundamental nature of the complexes.
Figure 4:
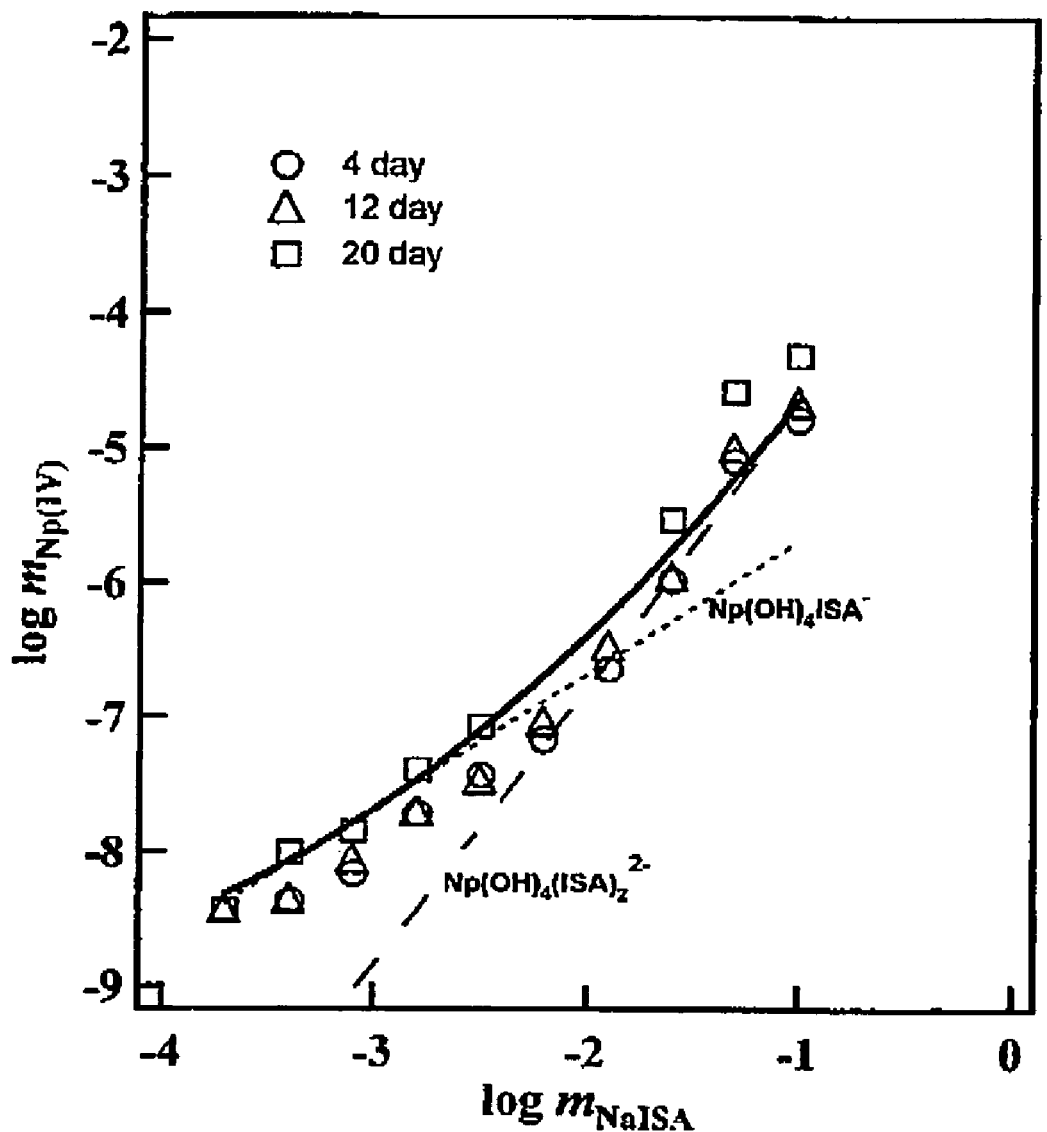
FIG. 4 is a graph of aqueous Np(IV) concentrations in equilibrium with $NpO_2(am)$ as a function of ISA concentrations at a fixed pH value of 12, showing the effectiveness of ISA in solubilizing Np(IV) even at high pH and showing the actual complexes that are important in this region.

The solubility of $NpO_2(am)$, the most dominant compound of tetravalent Np and an excellent analog for tetravalent Pu since Np is an adjacent actinide to Pu, as a function of pH at a fixed concentration of ISA shows that the observed aqueous Np concentrations are up to several orders of magnitude higher than expected in the absence of ISA (FIG. 3). As stated under Th above, the observed Np concentrations will increase with the increase in ISA concentrations. To further verify this and to develop further fundamental data, the solubility of NpO2(am) was also determined as a function of ISA concentrations at a fixed pH of 12 (FIG. 4). These data showed dramatic increases in solubility with the increase in ISA concentrations. In a fashion similar to Th, when the solubility as a function of ISA concentrations at a fixed pH of 12 (FIG. 4) are compared to the concentrations at a fixed pH of 5 (D. Rai, et al., "The Influence of Isosaccharinic Acid on the Solubility of Np(IV) Hydrous Oxide", *Radiochim. Acta* 83:9-13 (1998)), the dramatic increases in Np concentrations are observed in most of the environmental range of pH values with the increase in ISA concentrations. Since U and Pu are adjacent actinides to Np, behavior similar to that observed for Np will also be expected for tetravalent U and Pu.

Figure 5:
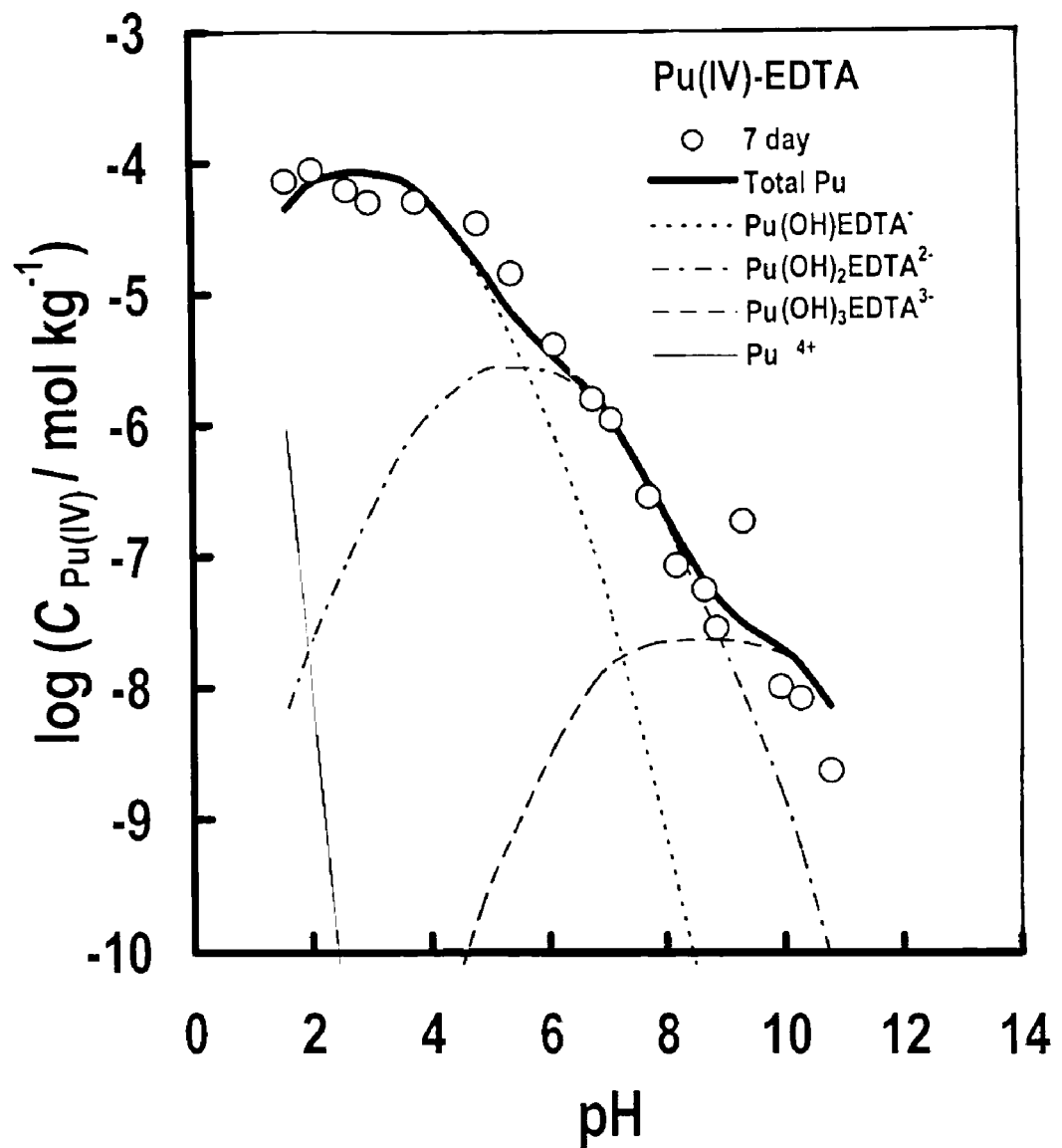
FIG. 5 is a graph of aqueous Pu(IV) concentrations in equilibrium with $PuO_2(am)$ as a function of pH and in the presence and absence of EDTA concentration of 0.0001M.
Figure 6:
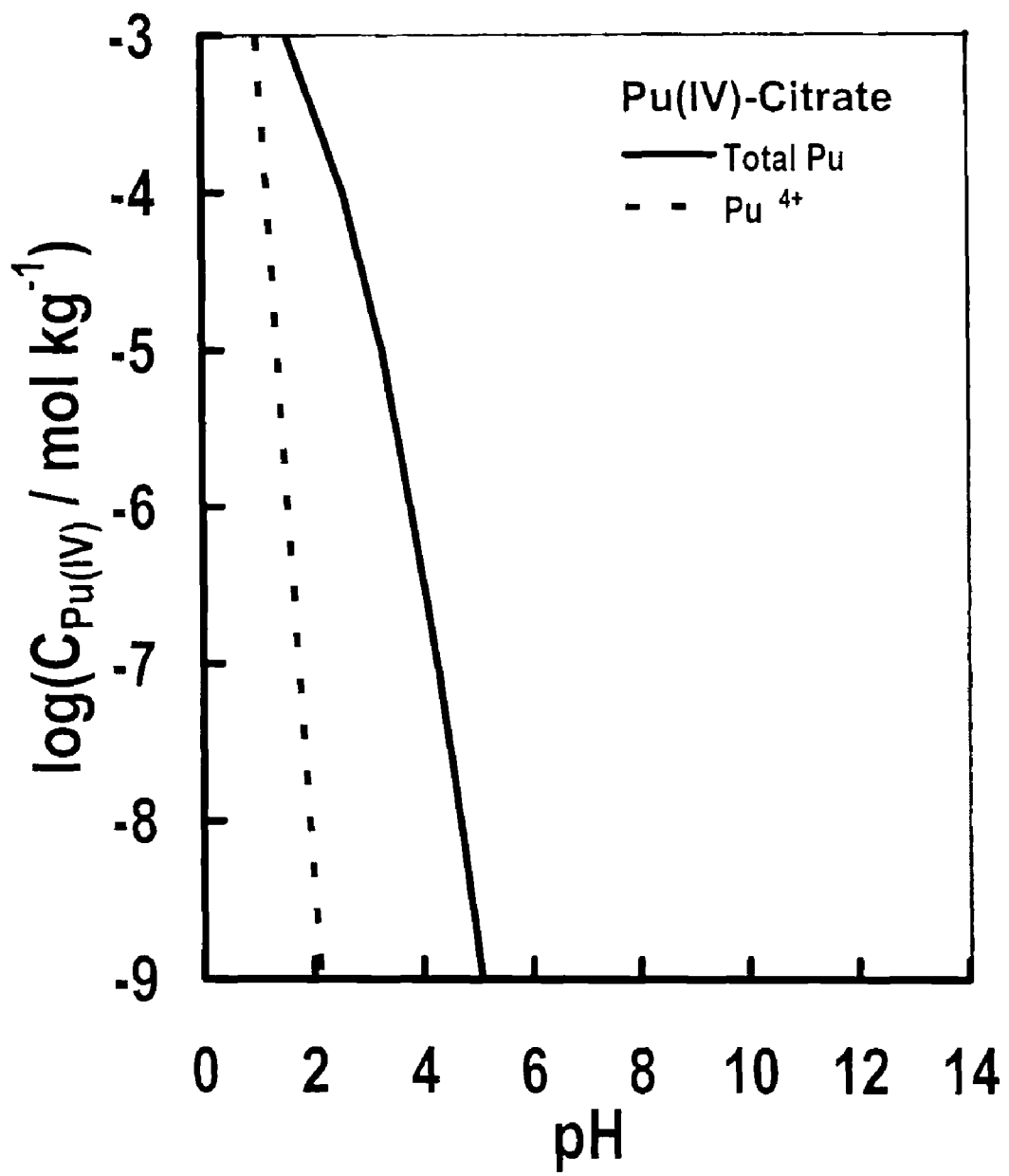
FIG. 6 is a graph of aqueous Pu(IV) concentrations in equilibrium with $PuO_2(am)$ as a function of pH and in the presence and absence of citrate concentration of 0.008 M showing that citrate can only be effective under very acidic conditions.

Even the most recent data for Pu(IV) complexes with EDTA (D. Rai, et al., "Thermodynamic Model for the Solubility of $PuO_2(am)$ in the Aqueous $Na^+$—$H^+$—$OH^-$—$Cl^-$—$H_2O$— Ethylenediaminetetraacetate System", *Radiochim. Acta* 89:67-74 (2001)) (FIG. 5), which show much stronger complexation constant values than previously reported, show that the Pu concentrations will decrease with the increase in pH as opposed to complexes with ISA that show either constant concentrations or increase in concentrations due to complexes of the type $An(OH)_4(ISA)_x^{-x}$ (where An stands for a tetravalent actinide). Also, citrate is effective in removing Pu(IV) in very acidic solutions only (FIG. 6). These fundamental data on Np(IV) and Th have helped develop a fundamental understanding of the ISA reactions in an environmentally important range of pH values and as a function of ISA concentrations such that chemical conditions necessary for foams and other media containing ISA for cleaning purposes can be well established based on scientific grounds.

The main conclusion to draw from all of the above data in conjunction with the empirical studies of Examples 1-3 is that ISA is far superior in removing actinides from contaminated surfaces as compared to EDTA, citrate, and oxalic acid (which, although data are not shown here, behave in a fashion similar to citrate), the most common currently-used chemicals. In addition, the currently-used chemicals are either very harsh, not environmentally friendly, or are fairly recalcitrant to biodegradation. ISA out-competes currently-used chemicals in all of these aspects.

Example 5

Figure 7:
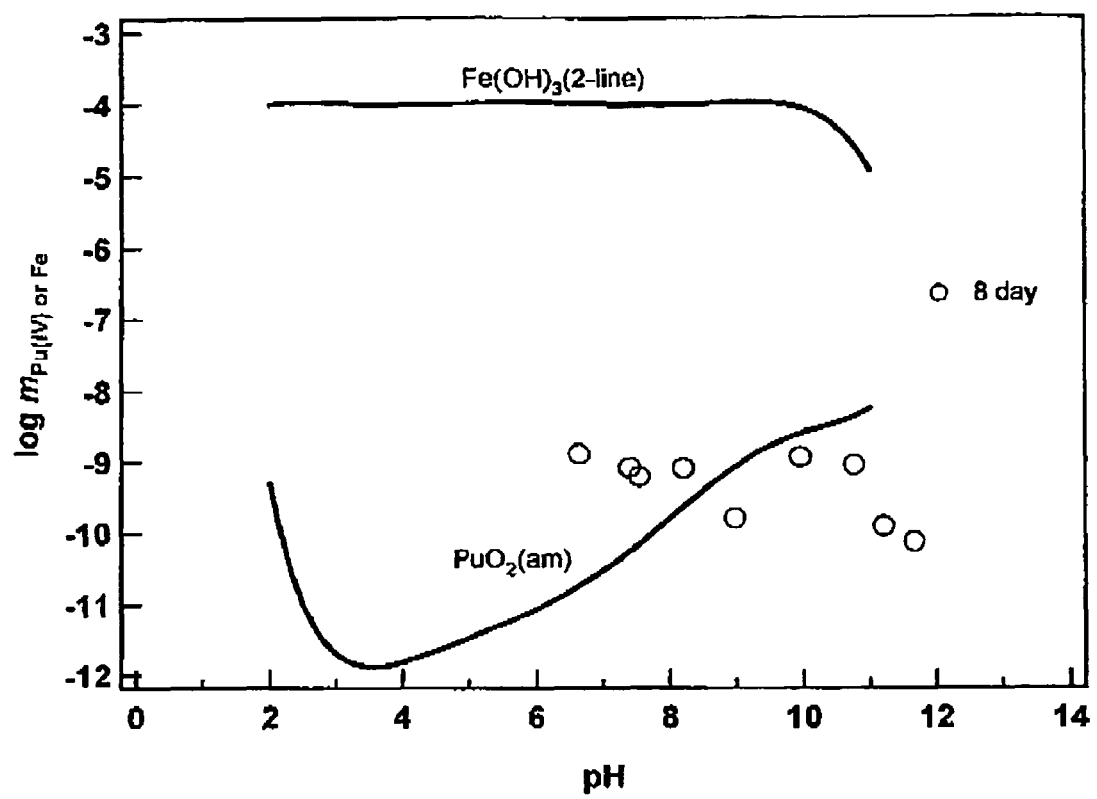
FIG. 7 is a graph of aqueous Pu(IV) concentrations in equilibrium with $PuO_2(am)$ and $Fe(OH)_3$ (2-line ferrihydrite) in the presence of 0.0001 M EDTA and as a function of pH, showing that EDTA in the presence of $Fe(OH)_3$ solid is not effective in solubilizing Pu, but is only effective in solubilizing Pu in a limited pH range in the absence of $Fe(OH)_3$ solid (compare FIG. 5)
Figure 8:
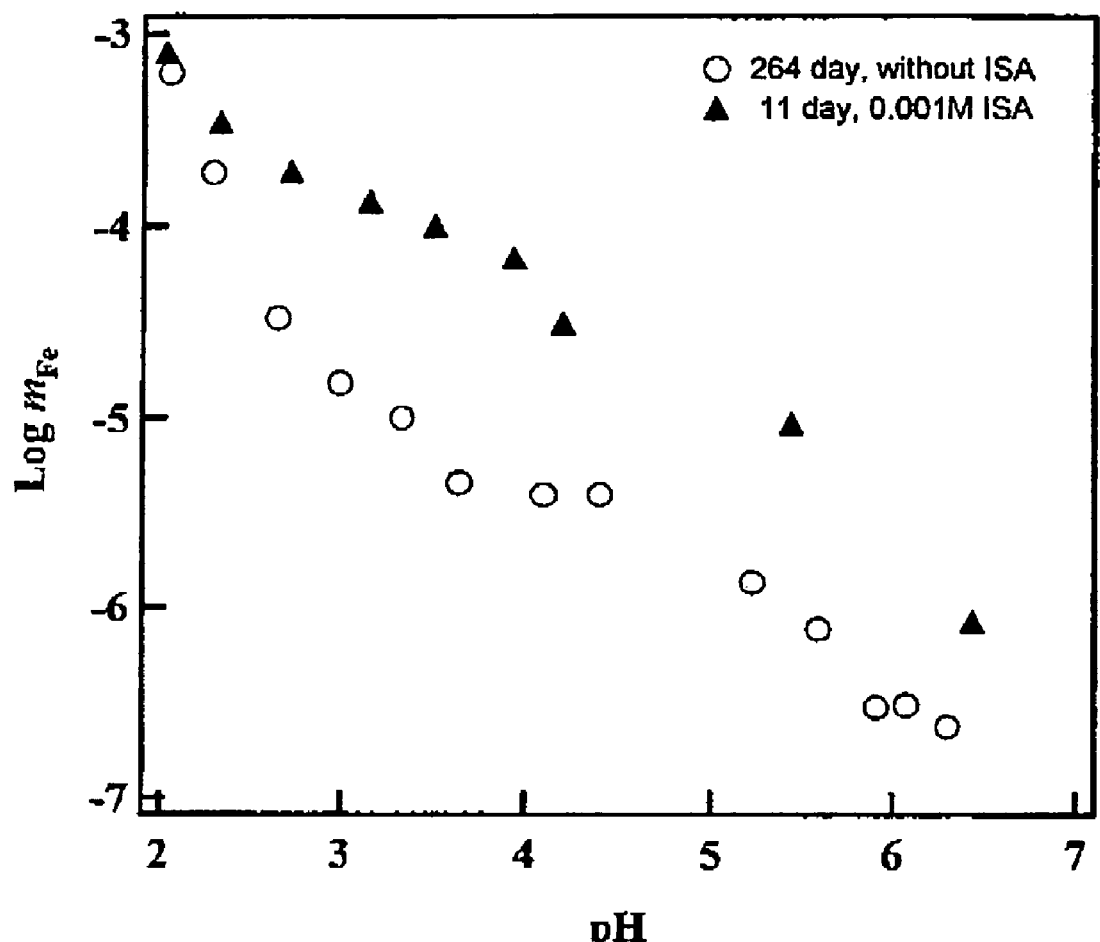
FIG. 8 is a graph of aqueous Fe(III) concentrations in equilibrium with $Fe(OH)_3$ (2-line ferrihydrite) in the absence and presence of ISA, showing that increase in ISA concentration will increase the solubility of Fe.

No data on ISA complexation with Fe(III) are available in the literature. These data are necessary for determining whether ISA will complex actinides in preference to Fe(III), which is ubiquitous in the natural environment. This is one of the biggest problems with existing decontaminating agents such as EDTA: EDTA strongly complexes Fe(III) in preference to tetravalent actinides in the entire range of environmentally important pH values, so that EDTA in the presence of Fe-containing substrates will not be effective in removing tetravalent actinides (FIG. 7). The data in FIG. 7 shows that EDTA (0.0001M) strongly binds with Fe(III), leaving it unavailable for complexation with Pu(IV). Thus the observed Pu(IV) concentrations are extremely low and near the detection limit. EDTA is not, therefore, an effective decontaminant for Pu, even though it is currently the most-used and preferred decontaminating agent. In contrast, ISA does not form as strong complexes with Fe(III) as EDTA (FIG. 8) but forms types of complexes with tetravalent actinides which are much more stable in the alkaline environment, and thus is more effective in binding with Pu and other actinides. However, ISA's complexes with Fe(III) are strong enough that it is an effective agent to remove Fe stains and rust from surfaces: especially considering that solubilization of Fe(III) can be enhanced by orders of magnitude by simply increasing the ISA concentrations. Similar data on the Ca complexes of ISA show that ISA is effective in removing hard water stains as well.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for preparing an acidic solution containing ISA (isosaccharinate), the method comprising the steps of:
   a) preparing a solution of $X_2CO_3$ and XOH;
   b) adding $Ca(ISA)_2$ to the solution from step a) and agitating, thereby precipitating solid $CaCO_3$ and leaving dissolved X(ISA) in solution;
   c) removing the solid $CaCO_3$ precipitate from the solution from step b), thereby leaving a solution containing dissolved X(ISA) and residual $X_2CO_3$ and XOH; and
   d) adjusting the pH of the solution from step c) to between approximately 4.5 to 5.0, thereby removing excess carbonate and hydroxide;
   wherein X is selected from the group consisting of Na and K.

2. The method of claim 1, wherein the step of adjusting the pH in step d) comprises adding HCl.

3. The method of claim 1 additionally comprising:
   e) adding $CaCl_2$ to the solution from step d), thereby precipitating solid purified $Ca(ISA)_2$.

4. The method of claim 3 additionally comprising:
   f) removing and washing the precipitated purified $Ca(ISA)_2$ from the solution from step e).

5. The method of claim 4 additionally comprising steps for producing very high purity $Ca(ISA)_2$ by repetitively removing $X_2CO_3$ and XOH impurities; wherein the additional steps comprise: repeating steps a) through f) one or more times; while reusing the precipitated purified $Ca(ISA)_2$ produced in step f) as the source of $Ca(ISA)_2$ material used in step b).

6. The method of claim 1, additionally comprising adding the solution from step d) to a foam, gel, or strippable coating.

7. The method of claim 1, wherein the acidic solution containing ISA additionally comprises one or more substances selected from the group consisting of: non-ISA organic chelators, inorganic chelators, carbonates, oxidizers, anti-freezes, and surfactants.

8. The method of claim 4, further comprising, after step f), recovering the washed precipitated purified $Ca(ISA)_2$ by evaporation or freeze-drying.

9. A method for preparing highly purified $Ca(ISA)_2$, the method comprising the steps of:
   a) preparing a solution of $X_2CO_3$ and XOH;
   b) adding $Ca(ISA)_2$ to the solution from step a) and agitating, thereby precipitating solid $CaCO_3$ and leaving dissolved X(ISA) in solution;
   c) removing the solid $CaCO_3$ precipitate from the solution from step b), thereby leaving a solution containing dissolved X(ISA) and residual $X_2CO_3$ and XOH;
   d) adjusting the pH of the solution from step c) to between approximately 4.5 to 5.0 by adding HCl, thereby removing excess carbonate and hydroxide;
   e) adding $CaCl_2$ to the solution from step d), thereby precipitating solid purified $Ca(ISA)_2$;
   f) removing and washing the precipitated purified $Ca(ISA)_2$ from the solution from step e); and
   g) repeating steps a) through f) one or more times; while reusing the precipitated purified $Ca(ISA)_2$ produced in step f) as the source of $Ca(ISA)_2$ material used in step b);
   wherein X is selected from the group consisting of Na and K.

* * * * *